United States Patent
Pan et al.

(10) Patent No.: US 11,516,999 B2
(45) Date of Patent: Dec. 6, 2022

(54) LIGHTING EXPERIMENTAL SYSTEM AND METHOD FOR REDUCING ABILITY OF POULTRY TO RECOGNIZE RED OBJECTS

(71) Applicant: ZHEJIANG UNIVERSITY, Hangzhou (CN)

(72) Inventors: Jinming Pan, Hangzhou (CN); Chenghao Pan, Hangzhou (CN); Yuchen Hu, Hangzhou (CN); Leshang Bai, Hangzhou (CN); Hao Jin, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 17/607,417

(22) PCT Filed: May 22, 2020

(86) PCT No.: PCT/CN2020/091727
§ 371 (c)(1),
(2) Date: Oct. 29, 2021

(87) PCT Pub. No.: WO2021/073091
PCT Pub. Date: Apr. 22, 2021

(65) Prior Publication Data
US 2022/0217954 A1    Jul. 14, 2022

(30) Foreign Application Priority Data

Dec. 25, 2019  (CN) .......................... 201911358661.0
Dec. 25, 2019  (CN) .......................... 201911360669.0

(51) Int. Cl.
*A01K 67/02*  (2006.01)
*A01K 45/00*  (2006.01)
(Continued)

(52) U.S. Cl.
CPC .............. *A01K 67/02* (2013.01); *A01K 45/00* (2013.01); *H05B 45/10* (2020.01); *H05B 45/20* (2020.01); *F21Y 2115/10* (2016.08)

(58) Field of Classification Search
None
See application file for complete search history.

(56) References Cited

U.S. PATENT DOCUMENTS

2015/0115845 A1*  4/2015  Grajcar .................... A01K 1/00
                                                                315/360

FOREIGN PATENT DOCUMENTS

CN       105028239 A      11/2015
CN       106489790 A      3/2017
(Continued)

OTHER PUBLICATIONS

Liu Jianzhu, et al., Special Economic Animal Disease Prevention and Control, 2014, pp. 246-247.
(Continued)

*Primary Examiner* — Anh Q Tran
(74) *Attorney, Agent, or Firm* — Bayramoglu Law Offices LLC (57) ABSTRACT

A lighting experimental system and a lighting experimental method for reducing the ability of the poultry to recognize the red objects are provided, wherein wooden testing box is provided with an opening at the top thereof, a square adjustable light-emitting diode (LED) light source is disposed directly above the opening of the wooden testing box, a first black backdrop is fixedly laid on a surface of each inner wall of four sides of the wooden testing box, a horizontal trough is provided at the bottom of the wooden testing box, a feed box is disposed in the horizontal trough, and the feed box is connected to an electric push rod; two color photographic papers are fixed on an inner wall, directly (Continued)

above the horizontal trough, of the wooden testing box, pressure sensors are disposed between the color photographic papers and the inner wall of the wooden testing box.

10 Claims, 2 Drawing Sheets

(51) Int. Cl.
 *H05B 45/20* (2020.01)
 *H05B 45/10* (2020.01)
 *F21Y 115/10* (2016.01)

(56) References Cited

FOREIGN PATENT DOCUMENTS

| | | | |
|---|---|---|---|
| CN | 110191531 A | * | 8/2019 |
| CN | 111066724 A | | 4/2020 |
| CN | 111067475 A | | 4/2020 |
| WO | WO-2021198681 A1 | * | 10/2021 |

OTHER PUBLICATIONS

Hao Zhengli, Chicken feed scientific preparation and application 2nd edition, 2013, pp. 219.

* cited by examiner

LIGHTING EXPERIMENTAL SYSTEM AND METHOD FOR REDUCING ABILITY OF POULTRY TO RECOGNIZE RED OBJECTS

CROSS REFERENCE TO THE RELATED APPLICATIONS

This application is the national phase entry of International Application No. PCT/CN2020/091727, filed on May 22, 2020, which is based upon and claims priority to Chinese Patent Application No. 201911360669.0 and No. 201911358661.0, both filed on Dec. 25, 2019, the entire contents of which are incorporated herein by reference.

TECHNICAL FIELD

The present disclosure relates to a detection method and system for the ability of poultry to recognize red objects, and in particular, to an ambient light-based system and method for a behavioral experiment of testing the ability of poultry to recognize red objects.

BACKGROUND

Poultry perceive external light stimuli mainly through their hypothalamic and retinal photoreceptors, which convert light signals into biological signals to cause their pituitary glands to release hormones, thereby regulating their daily activities, growth and development. Poultry's retinal photoreceptor cells are classified into three classes and six subclasses. The first class includes four types of single cones, which can adjust the color perception ability of the poultry, so that the poultry can perceive ultraviolet light and other light that humans cannot perceive. The second class is double cones, which can perceive object motion information. The third class is rods, which can perceive changes in light intensity under weak light. Compared with humans, chickens and other birds have superior visual functions as they have one more type of cones, and therefore, are more sensitive to a change in a light environment.

In recent years, with the increasing attention to animal welfare in breeding, behavioral research on animals has also received considerable attention. In terms of light information perception of animals, color recognition in poultry is gradually becoming an active area of research. Birds and humans are currently the known animals capable of classifying colors independently. However, color recognition in poultry is not only related to the color of an object to be recognized, but also closely related to the light color and light intensity of the ambient light, and even affected by an ambient sound and their mates. In bird research it has been proved that the color and brightness of eggshells have important implications for host birds to remove eggs of parasitic birds. This shows that a color difference between objects is critically important for birds to recognize the target object. Under specific ambient light, when a color difference between two objects is reduced to a certain extent, birds cannot distinguish between them. In addition, the light intensity of the ambient light will affect the birds' recognition on the object color, and even color recognition involves a lowest threshold for the light intensity of the ambient light.

Cannibalism in poultry generally refers to behaviors such as feather pecking, vent pecking or wing pecking, and is easily caused by environmental factors such as high stocking density, high temperature in the breeding house, high light intensity and poor ventilation, as well as nutritional factors such as low protein content and mineral imbalance in the feed. However, chickens and some other poultry have the habit of pecking red objects such as combs, vents, and blood. When an injured chicken is bleeding, it will attract other chickens to the injured chicken and peck at it. This pecking behavior can quickly escalate into a more severe form of cannibalism. Therefore, the control of cannibalism is critical to large-scale poultry breeding. At present, red light is typically used in breeding to prevent and control cannibalism, as it can generally keep the poultry calm and reduce their stress responses, thereby reducing the occurrence of cannibalism. However, the red light remains a broad concept now, and how to set the dominant wavelength and the light intensity of the red light is not clearly defined. Hence, it is necessary to explore a specific lighting condition that can effectively reduce the occurrence of cannibalism and meet the actual need of poultry breeding.

SUMMARY

The present disclosure is intended to provide a system and method for testing the ability of poultry to recognize red objects, to simulate red objects by using red photographic paper, create, by using a square light-emitting diode (LED) light source, test space in which light color and light intensity of ambient light are adjustable, and explore, through adaptation, training, and testing, impact of the ambient light on the recognition of the red objects by the poultry. This resolves the technical problem that it is impossible to carry out an experiment for the recognition of the red objects by poultry in the prior art, fills a gap in the industry, and provides an experimental tool to prevent and control cannibalism by using a light environment in poultry breeding.

The technical solutions used in the present disclosure to resolve the technical problem thereof are as follows:

1. Lighting experimental system for reducing the ability of poultry to recognize red objects:

The system includes a wooden testing box, black polyvinyl chloride (PVC) backdrops, a square adjustable LED light source, color photographic papers, pressure sensors, a feed box, an electric push rod, and a feces receiving cloth, where the wooden testing box is a square wooden box provided with an opening at the top thereof, the square adjustable LED light source is disposed directly above the opening of the wooden testing box, a first black PVC backdrop is fixedly laid on a surface of each inner wall of four sides of the wooden testing box, and the gray feces receiving cloth is laid at the bottom of the wooden testing box; a horizontal trough is disposed at the bottom of an inner wall on one side of the wooden testing box, the feed box is disposed in the horizontal trough, the feed box is connected to the electric push rod, the electric push rod pushes the feed box to move horizontally to drive the feed box into the wooden testing box or out of the wooden testing box through the horizontal trough; two color photographic papers are fixed on the inner wall, directly above the horizontal trough, of the wooden testing box, the pressure sensors are disposed between the color photographic papers and the inner wall of the wooden testing box, and the two color photographic papers are pure-color photographic papers of different colors; and a second black PVC backdrop for blocking is disposed outside the inner wall, on which the two color photographic papers are fixed, of the wooden testing box.

The upper end of the second black PVC backdrop is connected to and mounted on a lifting mechanism, and the second black PVC backdrop is driven by the lifting mechanism to move down to block and cover the two color photographic papers or move up not to block and cover the two color photographic papers.

The two color photographic papers are pasted horizontally and symmetrically on the inner wall of the wooden testing box and are located at two upper sides of the feed box.

The system is used for lighting during indoor broiler breeding, but is not limited thereto.

Poultry feed is placed in the feed box.

Feed is pasted in a center of each of the color photographic papers when training.

Based on the above system in the present disclosure, it is found that there is a relationship between a lighting condition of a light source and the ability of poultry to recognize red objects. Based on this relationship, a special light source is used to provide lighting for the poultry, to reduce the occurrence of cannibalism such as vent pecking or feather pecking of the poultry, and improve efficiency and productivity of poultry breeding.

2. A lighting experimental method for reducing the ability of poultry to recognize red objects by using the detection system according to claim 1 includes:

a detection process, wherein the detection process includes adaptation, training, and testing in the sequence as follows:

1) adaptation:

placing a red photographic paper with an RGB color (255, 0, 0) and a yellow photographic paper with an RGB color (255, 255, 0), performing lighting by using the square adjustable LED light source to provide ambient light, and putting poultry into the wooden testing box for a period of time to enable them to adapt to an internal closed environment;

2) training:

2.1) early training:

on a first day, pasting a grain of feed on a surface of each of the two color photographic papers by using an adhesive tape, and putting a little feed into the feed box, and training, by a food reward method, the poultry to recognize the red photographic paper; and when the poultry peck the red photographic paper, pushing, by the electric push rod, the feed box into the wooden testing box through the horizontal trough to allow the poultry to peck the feed for 4 s, and then pulling, by the electric push rod, the feed box out of the wooden testing box to prevent the poultry from pecking the feed; or when the poultry peck the yellow photographic paper, disabling the electric push rod, and giving no feed reward; and removing the feed on the surface of each of the two color photographic papers after the poultry have correctly recognized the red photographic paper for three times, and then performing later training on the poultry; and 2.2) later training:

blocking the two color photographic papers by using one second black PVC backdrop, quickly removing the second black PVC backdrop after maintaining or reversing positions of the two color photographic papers, observing responses of the poultry to the two color photographic papers, and determining whether the poultry recognize and peck the red photographic paper; and repeating the training until the poultry can recognize the red photographic paper for ten consecutive times;

3) testing:

keeping the red photographic paper unchanged, and successively replacing the original yellow photographic paper with the RGB color (255, 255, 0) by a plurality of photographic papers whose G components in RGB color space are sorted in descending order, to make colors of paired photographic papers gradually approximate to the red color; and after each replacement, performing the late training in step 2.2), repeating the testing for twelve times, and recording the results of last ten times indicating whether the poultry accurately recognize the red photographic paper in each test, to obtain the accuracy of recognizing the red photographic paper by the poultry under specific ambient light, and determine impact of the ambient light on the recognition of the red objects by the poultry.

In the testing in step 3), RGB colors of the plurality of photographic papers whose G components in the RGB color space are sorted in descending order are (255, 219, 0), (255, 182, 0), (255, 146, 0), (255, 109, 0), (255, 73, 0), and (255, 36, 0), respectively.

Before the training and testing, the poultry are kept hungry.

The poultry can be fed only when the experiment is being carried out, after the poultry complete the experiment and before the experiment on the same day ends, and within half an hour after the end of the experiment on the same day.

The poultry are, but not limited to, chickens.

3. Lighting method for reducing the ability of poultry to recognize red objects, comprising:

providing ambient light by using a special light source to perform lighting/breeding for poultry, wherein the special light source provides warm white light with a color temperature lower than 3000 K and a light intensity ranging from 2 lux to 50 lux, so that the lighting can reduce the ability of the poultry to recognize red objects.

The ability of the poultry to recognize the red objects is reduced to reduce the occurrence of cannibalism such as vent pecking or feather pecking of the poultry.

Lamps for the lighting include but are not limited to an incandescent lamp, a LED lamp, an organic LED (OLED) lamp, a quantum dot-based LED lamp, and a fluorescent lamp.

The poultry are, but not limited to, chickens.

The lighting for the poultry is used for indoor broiler breeding.

The present disclosure designs a complete set of experimental detection apparatuses and methods for animal behavior, including: adaptation, training, and testing. The adaptation is mainly performed to reduce stress generated by the poultry in the detection. During the training, the food reward method is used to train the poultry to make specific behavior (recognize the red objects in this experiment). During the testing, whether the poultry can still make specific behavior (accuracy of recognizing the red objects in this experiment) is tested.

The poultry like to peck red objects such as combs, vents, and blood. The present disclosure simulates the red objects by using the red photographic paper, to obtain impact of a light color and a light intensity of the ambient light on the recognition of the red objects by the poultry. This prevents cannibalism by using a light environment in poultry breeding, and improves efficiency of poultry breeding.

Based on the above experimental detection apparatus and method in the present disclosure, it is found that there is a relationship between a lighting condition of a light source and the ability of the poultry to recognize the red objects. Based on this relationship, a special light source is used to provide lighting for the poultry, to reduce cannibalism such as vent pecking or feather pecking of the poultry, and improve efficiency and productivity of poultry breeding.

The present disclosure has the following beneficial effects:

1. In the method of the present disclosure, a modulation spectrum range of the square LED light source used in the experimental detection is 350 nm to 800 nm, which basically covers a light sensitive band of the poultry, and the light intensity is linearly adjustable. The square behavior experimental region provides ambient light with uniform horizontal light intensity and free from stroboflash.

2. The present disclosure can be used to detect the impact of the light color and the light intensity of the ambient light on the recognition of the red objects by the poultry, and study ambient light that can reduce the ability of the poultry to recognize the red objects, thereby providing an experimental tool to prevent and control cannibalism by using the light environment in poultry breeding.

3. The lighting method provided in the present disclosure uses the special light source to provide the ambient light used by the poultry to recognize the red objects. This can effectively reduce the accuracy of recognizing the red objects by the poultry, and further reduce the occurrence of cannibalism such as vent pecking.

The lighting method also can effectively reduce dust in the environment, improve air quality, reduce the occurrence of a respiratory disease, and reduce mortality of the poultry.

Table 1 shows impact of a color difference (represented by G components of paired photographic papers, where a larger G component leads to a larger color difference) of the paired photographic papers on the recognition of red objects by the poultry under low (2 lux), medium (20 lux), and high (50 lux) light intensities.

Figure 1:
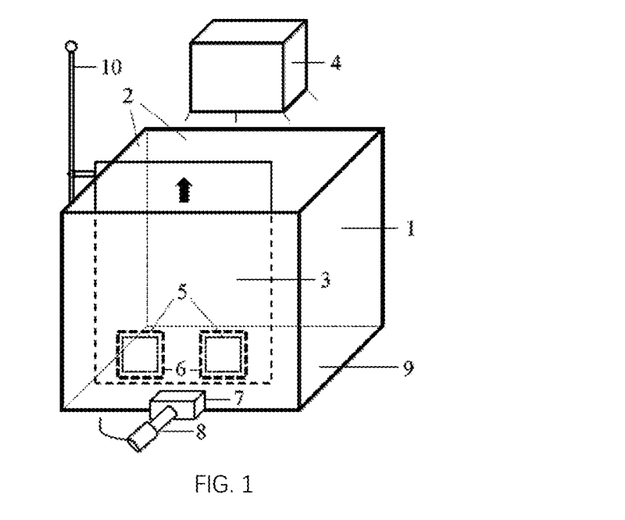
FIG. 1 is a schematic structural diagram of a detection system according to the present disclosure.

In FIG. 1: 1: wooden testing box; 2: first black PVC backdrop; 3: second black PVC backdrop; 4: square adjustable LED light source; 5: color photographic papers; 6: pressure sensor; 7: feed box; 8: electric push rod; 9: feces receiving cloth; 10: lifting mechanism.

DETAILED DESCRIPTION OF THE EMBODIMENTS

The present disclosure is described in further detail below with reference to the accompanying drawings and embodiments.

Embodiment 1

A detection system is placed in a darkroom environment. As shown in FIG. 1, the system specifically includes a wooden testing box 1, black PVC backdrops 2 and 3, a square adjustable LED light source 4, color photographic papers 5, pressure sensors 6, a feed box 7, an electric push rod 8, and a feces receiving cloth 9. The wooden testing box 1 is a square wooden box whose internal space is 50 cm×50 cm×50 cm. The wooden testing box 1 is provided with an opening at the top thereof, from which tested poultry are put into the wooden testing box 1. The square adjustable LED light source 4 is disposed directly above the opening of the wooden testing box 1 to provide ambient light. The first black PVC backdrop 2 is fixedly laid on a surface of each inner wall of four sides of the wooden testing box 1 to reduce reflections. The gray feces receiving cloth 9 is laid at the bottom of the wooden testing box 1. A horizontal trough is disposed at the bottom of an inner wall on one side of the wooden testing box 1, the feed box 7 is disposed in the horizontal trough, the feed box 7 is connected to the electric push rod 8, and the electric push rod 8 is located outside the wooden testing box 1. The electric push rod 8 pushes the feed box 7 to move horizontally to drive the feed box 7 into the wooden testing box 1 or out of the wooden testing box 1 through the horizontal trough. Two color photographic papers 5 are fixed on the inner wall, directly above the horizontal trough, of the wooden testing box 1, and the color photographic papers 5 is 18 cm away from the ground and is 10 cm×10 cm in size. The pressure sensors 6 are disposed between the color photographic papers 5 and the inner wall of the wooden testing box 1, and it is detected whether the poultry peck the color photographic papers 5 based on a pressure jump of the pressure sensors 6. The two color photographic papers (5) are pure-color photographic papers of different colors, and are pasted horizontally and symmetrically on the inner wall of the wooden testing box 1 and are located at two upper sides of the feed box 7. The second black PVC backdrop 3 for blocking is disposed outside the inner wall, on which the two color photographic papers 5 are fixed, of the wooden testing box 1.

In specific implementation, the photographic paper is inserted into a photo slot, so that the photographic paper of various colors can be taken out of the photo slot or put into the photo slot at any time.

The feed box 7 below the color photographic papers 5 is pushed into the wooden testing box 1 through the horizontal trough to feed the poultry. The feed box is drawer-shaped, with a length, a width and a height being 16 cm, 10 cm, and 6 cm respectively. The feed box is usually pulled out of the wooden testing box, and can be used to feed the poultry after being completely pushed into the wooden testing box. After the poultry in the wooden testing box 1 peck the red photographic paper, the switch of the electric push rod 8 is pressed, and the feed box 7 is pushed into the wooden testing box to feed the poultry, and automatically exits the wooden box after specified time.

Figure 3:
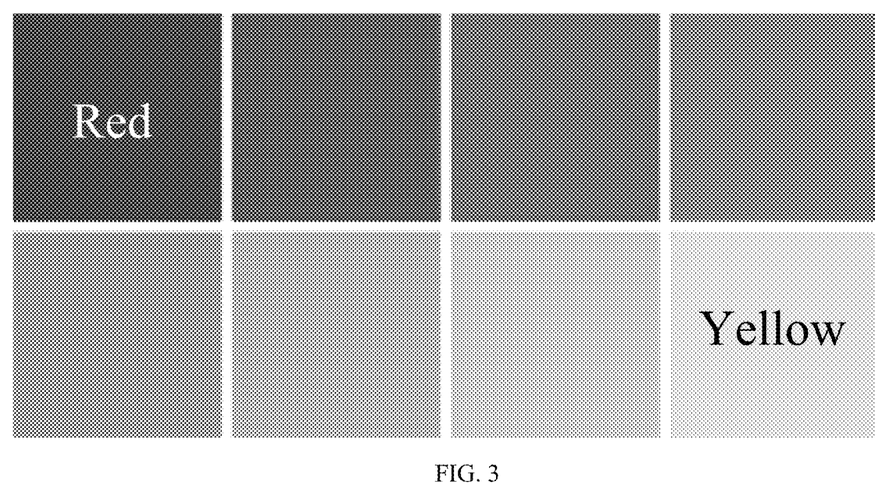
FIG. 3 is a schematic diagram of eight types of photographic paper used in Embodiment 1, where the number represent an RGB value of a color.

As shown in FIG. 3, there are a total of eight RGB values for the photographic paper, namely, (255, 0, 0), (255, 36, 0), (255, 73, 0), (255, 109, 0), (255, 146, 0), (255, 182, 0), (255, 219, 0), and (255, 255, 0). An RGB value is (255, 0, 0) for the red photographic paper and (255, 255, 0) for the yellow photographic paper.

Figure 2:
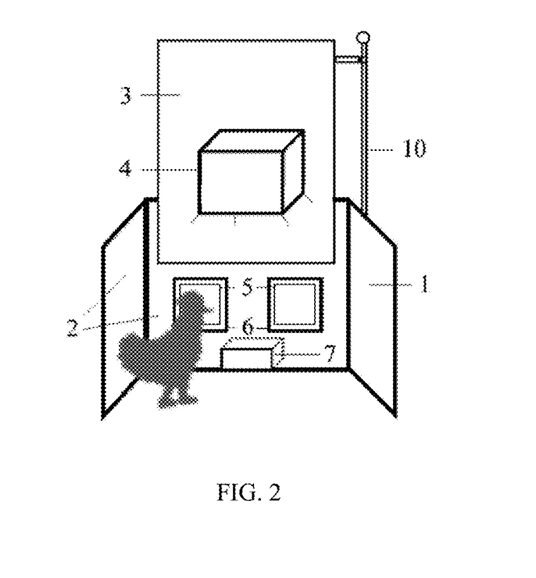
FIG. 2 is a schematic diagram of an internal real layout of a detection system according to the present disclosure.

As shown in FIG. 2, in specific implementation, the second black PVC backdrop 3 is connected to and mounted on a lifting mechanism, and the lifting mechanism 10 can drive the second black PVC backdrop 3 move up and down. The second black PVC backdrop 3 is driven by the lifting mechanism 10 to move down to block and cover the two color photographic papers 5 or move up not to block and cover the two color photographic papers 5. In specific implementation, the second black PVC backdrop 3 is quickly moved upward and removed, and responses of the poultry to the paired photographic papers can be observed.

In specific implementation, light color and light intensity of the light source are also adjusted to ensure that a light color and a light intensity measured by a spectroradiometer in a center that is of the box and that is 18 cm away from the ground meet requirements respectively, and data are saved in a light source controller for subsequent call. A height above the ground is set to 18 cm, which is equal to eyeball heights of the poultry when the poultry walk normally.

When the above detection system is used, a detection process includes adaptation, training, and testing in sequence.

1) Adaptation

The red photographic paper with the RGB color (255, 0, 0) and the yellow photographic paper with the RGB color (255, 255, 0) are placed, lighting is performed by using the ambient light through the square adjustable LED light source 4, and the poultry is put into the wooden testing box 1 in sequence for a period of time to enable them to adapt to an internal closed environment, to reduce impact of stress on the detection.

The adaptation is further divided into adaptation to a breeding environment and adaptation to a testing environment.

Poultry with a basically same weight are selected and randomly divided into several groups according to different light intensities or light colors. Since the poultry used in the experiment are generally kept in captivity, stress may be easily generated when they are just put into a new environment, and may affect subsequent behavioral detection. During breeding, sufficient feed and water are provided every day to make the poultry fully adapt to the new breeding environment. This stage lasts about three days.

Then, the adaptation to the detection environment is performed in a darkroom to make the poultry no longer flutter and chirp in the wooden box. The red photographic paper with the RGB color (255, 0, 0) and the yellow photographic paper with the RGB color (255, 255, 0) are placed, lighting is performed by using the ambient light through the square adjustable LED light source 4, and the poultry is put into the wooden testing box 1 in sequence for a period of time to enable them to adapt to an internal closed environment, to reduce impact of stress on the detection. The adaptation is performed on the poultry once a day for ten min for two days. In this case, only a few poultry may peck the slot with the red photographic paper, and the switch of the electric push rod is pressed to push the feed box into the wooden testing box to feed the poultry.

2) Training

Before the training, the poultry are kept hungry. A setting of the light color and the light intensity is the same as that in the adaptation process.

2.1) Early training

On a first day, a grain of feed is pasted on a surface of each of the two color photographic papers 5 by using an adhesive tape, and a little feed is put into the feed box 7 that can be pushed into the wooden testing box by the electric push rod, to feed the poultry. The poultry is trained by a food reward method, to recognize the red photographic paper. As shown in FIG. 2, when it is detected by the pressure sensors that the poultry peck the red photographic paper, the electric push rod 8 pushes the feed box 7 into the wooden testing box 1 through the horizontal trough to allow the poultry to peck the feed for 4 s. Then, the electric push rod 8 drives the feed box 7 to move out of the wooden testing box 1 to prevent the poultry from pecking the feed, or the feed box 7 is automatically pushed out of the wooden testing box 1 after the specified time. When the poultry peck the yellow photographic paper, the electric push rod 8 does not work, and no feed reward is given. If the poultry peck another position, they are continuously observed for corresponding responses.

The poultry is trained for 5 min to 15 min every day, which lasts about two days. During this period, poultry that have not pecked the slot with the red photographic paper should be removed. The feed on the surface of each of the two color photographic papers 5 is removed after the poultry have correctly recognized the red photographic paper 3 for three times, and then later training is performed on the poultry.

2.2) Later training

The two color photographic papers 5 are blocked by using one second black PVC backdrop 3, the second black PVC backdrop 3 is removed quickly after positions of the two color photographic papers 5 are maintained or reversed, responses of the poultry to the two color photographic papers 5 are observed, and whether the poultry recognize and peck the red photographic paper is determined. The training is repeated until the poultry can recognize the red photographic paper for ten consecutive times. The position of the red photographic paper shall be changed at least four times for the ten times of training, and this stage lasts about two days.

3) Testing: A setting of the light color and the light intensity is the same as that in the adaptation process.

The red photographic paper keeps unchanged, and the original yellow photographic paper with the RGB color (255, 255, 0) is successively replaced by a plurality of photographic papers whose G components in RGB color space are sorted in descending order, to make colors of paired photographic papers gradually approximate to the red color. RGB colors of the plurality of photographic papers are (255, 219, 0), (255, 182, 0), (255, 146, 0), (255, 109, 0), (255, 73, 0), and (255, 36,0), respectively. These six colors are named test colors 1 to 6 in turn. For example, an RGB value of the test color 1 is (255, 219, 0), and an RGB value of the test color 6 is (255, 36, 0).

After each replacement, the late training in step 2.2) is performed, the testing is repeated for twelve times, and the results of last ten times indicating whether the poultry accurately recognize the red photographic paper is recorded in each test, to obtain the accuracy of recognizing the red photographic paper by the poultry under specific ambient light, and determine impact of the ambient light on the recognition of red objects by the poultry.

In this way, in addition to the red photographic paper and the yellow photographic paper, there are six types of photographic paper that each are paired with the red photographic paper. Two pairs of photographic paper are tested every day. This stage lasts about three days.

The poultry are supplied with sufficient water throughout the feeding process. However, to prevent the failure of the food reward method, the poultry need to be kept hungry in the training and test processes. The poultry can be fed only when the experiment is being carried out, after the poultry complete the experiment and before the experiment on the same day ends, and within half an hour after the end of the experiment on the same day.

After completing the test for each light intensity under a certain light color or each light color under a certain light intensity, the light color or the light intensity can be changed for a new round of detection, but the process only includes the same later training and testing. Because the detected objects are the same batch of poultry, it generally takes only one day to perform later training in the new round of detection. After the training, three-day testing is also performed.

Generally, two to three light colors or light intensities are set, to control daily experimental time to be within half a day, so as to reduce interference of a day and night rhythm to the experiment. Time required for each stage of the detection process is only an estimate, which may change slightly as a quantity of groups increases or decreases.

Example in the Present Disclosure

In this example, 21 8-week-old yellow feather broilers with similar body sizes are selected for research, and light colors 6500 K and 2700 K are selected. Based on low (2 lux), medium (20 lux), and high (50 lux) light intensities, the broilers are randomly divided into three groups with seven broilers in each group. Two broilers with poor performance in training are removed from a group corresponding to each light intensity, so five broilers in each group are tested. The whole experiment under a certain light environment lasts 12 days, including five-day adaptation, four-day training, and three-day testing.

Results are as shown in the following table.

Table 1 Impact of a color difference between paired photographic papers on the recognition accuracy

| Group | Color temperature | Light intensity | Accuracy of recognizing the red photographic paper ||||||
|---|---|---|---|---|---|---|---|---|
| | | | Test color 1 | Test color 2 | Test color 3 | Test color 4 | Test color 5 | Test color 6 |
| Experimental group 1 | 6500 K | 2 lux | 0.86 | 0.8 | 0.68 | 0.68 | 0.75 | 0.46 |
| Experimental group 2 | | 20 lux | 0.95 | 0.75 | 0.85 | 0.6 | 0.58 | 0.56 |
| Experimental group 3 | | 50 lux | 0.96 | 0.76 | 0.8 | 0.68 | 0.54 | 0.54 |
| Control group 1 | 2700 K | 2 lux | 0.8 | 0.62 | 0.56 | 0.58 | 0.42 | 0.48 |
| Control group 2 | | 20 lux | 0.9 | 0.73 | 0.63 | 0.63 | 0.43 | 0.5 |
| Control group 3 | | 50 lux | 0.84 | 0.72 | 0.6 | 0.5 | 0.44 | 0.46 |

The results show that a recognition rate of the broiler for the red photographic paper decreases gradually as colors of paired photographic papers gradually approximate to the red color ($P<0.05$). In terms of the light color, compared with broilers under 6500K ambient light, the broilers under 2700K light had lower recognition rates ($P<0.001$). In terms of the light intensity, there was no significant difference between recognition rates of the broilers for the red photographic paper under 2 lux, 20 lux, and 50 lux ambient light ($P>0.05$).

There is no significant difference between the red recognition rates under 2 lux to 50 lux ambient light, which may be possibly caused by that the light intensity of the ambient light does not reach a threshold. When the light intensity is reduced to a certain extent, it may affect the recognition rate of the red photographic paper.

Through the experiment by using the apparatus and the method in the present disclosure, it is found that a special light source can be used to provide the ambient light to perform lighting/breeding for the poultry. The special light source provides warm white light with a color temperature lower than 3000 K and a light intensity ranging from 2 lux to 50 lux, and can reduce the ability of the poultry to recognize the red objects, and further weaken the ability of the poultry to recognize red parts such as combs, vents, and injured parts, thereby reducing the occurrence of cannibalism such as vent pecking or feather pecking.

Therefore, it can be seen that through the experiment carried out by using the detection system, the present disclosure can be used to detect impact of the ambient light on the recognition of the red objects by the poultry, and provides an experimental tool to prevent and control cannibalism by using a light environment in poultry breeding.

Embodiment 2

The apparatus shown in Embodiment 1 is built.

Figure 4:
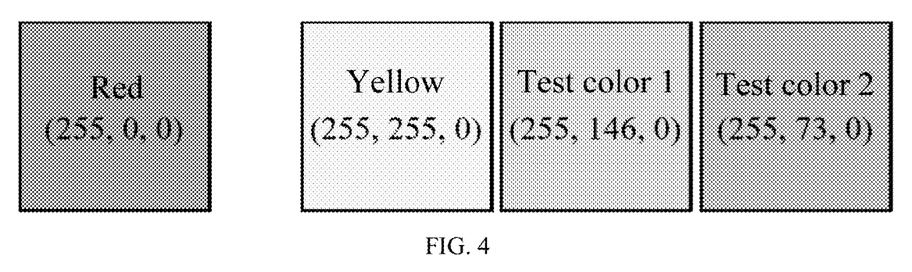
FIG. 4 shows photographic paper of four colors used in Embodiment 2, where an RGB value of the red photographic paper is (255, 0, 0), an RGB value of the yellow photographic paper is (255, 255, 0), an RGB value of the photographic paper of a test color 1 is (255, 146, 0), and an RGB value of the photographic paper of a test color 2 is (255, 73, 0).

As shown in FIG. 4, there is photographic paper 4 of four RGB values. An RGB value is (255, 0, 0) for red photographic paper, (255, 255, 0) for yellow photographic paper, (255, 146, 0) for photographic paper of a test color 1, and (255, 73, 0) for photographic paper of a test color 2. Two photographic papers 4 placed in two photo slots 3 are pure-color photographic papers of different colors. One piece of photographic paper 4 must be the red photographic paper (255, 0, 0), and an RGB value of the other piece of photographic paper 4 must be one of (255, 73, 0), (255, 146, 0) and (255, 255, 0).

In specific implementation, a color temperature is 2700 K for an experimental group and 6500 K for a control group, and three light intensities are specified for each group, namely, 2 lux, 20 lux, and 50 lux. The light intensity is measured in a center that is of a wooden box and that is 18 cm away from the ground.

In specific implementation, an experiment process includes adaptation, training, and testing in sequence.

Firstly, 20 8-week-old yellow feather broilers with similar body sizes are selected for research. Before the experiment, the broilers are successively put into the wooden box for adaptation, to reduce stress responses of broilers to a strange environment.

During the training, the red photographic paper and the yellow photographic paper are inserted into the slots, the broilers are trained by a food reward method, and feed is given to the broilers after the broilers peck the photo slot with the red photographic paper. The training is finished after the broilers can recognize the red photographic paper from paired red and yellow photographic papers for ten consecutive times.

During the testing, the red photographic paper (255, 0, 0) is kept unchanged, and the matching yellow photographic paper (255, 255, 0) is replaced by the photographic paper of the test color 1 and the photographic paper of the test color 2 in turn, to obtain the accuracy of recognizing the red photographic paper by the broiler under corresponding ambient light, as shown in the table below.

TABLE 2

Impact of a color difference of paired photographic papers on the recognition accuracy

| Group | Color temperature | Light intensity | Accuracy of recognizing the red photographic paper | |
|---|---|---|---|---|
| | | | Test color 1 (large color difference) | Test color 2 (small color difference) |
| Experimental group 1 | 2700 K | 2 lux | 0.56 | 0.42 |
| Experimental group 2 | | 20 lux | 0.63 | 0.43 |
| Experimental group 3 | | 50 lux | 0.6 | 0.44 |
| Control group 1 | 6500 K | 2 lux | 0.68 | 0.72 |
| Control group 2 | | 20 lux | 0.85 | 0.58 |
| Control group 3 | | 50 lux | 0.8 | 0.54 |

In Table 2, the color temperature of the ambient light is 2700 K for the experimental group and 6500 K for the control group, and three light intensities are specified for each group, namely, 2 lux, 20 lux, and 50 lux. An RGB value of the photographic paper of the test color 1 is (255, 146, 0), which is quite different from that of the red photographic paper. An RGB value of the photographic paper of the test color 2 is (255, 73, 0), which is slightly different from that of the red photographic paper.

The above results show that a recognition rate of the broiler for the red photographic paper decreases gradually as colors of paired photographic papers gradually approximate to the red color ($P<0.05$). In terms of the light color, compared with the color temperature 6500 K, the ambient light with the color temperature of 2700 K can effectively reduce the accuracy of recognizing the red objects by the broiler ($P<0.001$). However, for both the experimental group and the control group, the ambient light of 2 lux, 20 lux, and 50 lux has no significant effect on the recognition of the red objects by the broilers ($P>0.05$).

Compared with the group with the color temperature of 6500 K, a LED spectrum of the group with the color temperature of 2700 K contains richer red light components. Therefore, the recognition rate of the red photographic paper by the broilers in the group with the color temperature of 2700 K is significantly reduced. This means that the broilers may not easily find the red objects under red light, thereby reducing cannibalism.

The above specific implementations are used to explain the present disclosure, rather than to limit the present disclosure. Within the spirit of the present disclosure and the protection scope of the claims, any modification and change to the present disclosure should fall into the protection scope of the present disclosure.

What is claimed is:

1. A lighting experimental system for reducing an ability of poultry to recognize red objects, comprising:
    a wooden testing box,
    black polyvinyl chloride (PVC) backdrops,
    a square adjustable light-emitting diode (LED) light source,
    color photographic papers,
    pressure sensors,
    a feed box,
    an electric push rod, and
    a feces receiving cloth, wherein
    the wooden testing box is a square wooden box provided with an opening at a top thereof,
    the square adjustable LED light source is disposed directly above the opening of the wooden testing box,
    a first black PVC backdrop is fixedly laid on a surface of each inner wall of four sides of the wooden testing box, and the gray feces receiving cloth is laid at a bottom of the wooden testing box;
    a horizontal trough is disposed at a bottom of an inner wall on one side of the wooden testing box,
    the feed box is disposed in the horizontal trough, the feed box is connected to the electric push rod, the electric push rod pushes the feed box to move horizontally to drive the feed box into the wooden testing box or out of the wooden testing box through the horizontal trough;
    two color photographic papers are fixed on the inner wall, directly above the horizontal trough of the wooden testing box,
    the pressure sensors are disposed between the two color photographic papers and the inner wall of the wooden testing box, and the two color photographic papers are pure-color photographic papers of different colors; and
    a second black PVC backdrop for blocking is disposed outside the inner wall, on which the two color photographic papers are fixed, of the wooden testing box.

2. The lighting experimental system for reducing the ability of the poultry to recognize the red objects according to claim 1, wherein the second black PVC backdrop is connected to and mounted on a lifting mechanism, and the second black PVC backdrop is driven by the lifting mechanism to move down to block and cover the two color photographic papers or move up not to block and cover the two color photographic papers.

3. The lighting experimental system for reducing the ability of the poultry to recognize the red objects according to claim 1, wherein the two color photographic papers are pasted horizontally and symmetrically on the inner wall of the wooden testing box and are located at two upper sides of the feed box.

4. The lighting experimental system for reducing the ability of the poultry to recognize red objects according to claim 1, wherein the detection system is used for lighting during indoor broiler breeding.

5. The lighting experimental system for reducing the ability of the poultry to recognize the red objects according to claim 1, wherein poultry feed is placed in the feed box.

6. The lighting experimental system for reducing the ability of the poultry to recognize the red objects according to claim 1, wherein feed is pasted in a center of each of the color photographic papers when training.

7. A lighting experimental method for reducing an ability of poultry to recognize red objects by using the detection system of claim 1, comprising a detection process, wherein the detection process comprises adaptation, training, and testing in sequence:
    1) The adaptation comprises:
        placing a red photographic paper with an RGB color (255, 0, 0) and a yellow photographic paper with an RGB color (255, 255, 0), performing lighting by using the square adjustable LED light source to provide an ambient light, and putting the poultry into the wooden testing box in sequence for a period of time to enable the poultry to adapt to an internal closed environment;

2) The training comprises:

2.1) early training:

on a first day, pasting a grain of feed on a surface of each of the two color photographic papers by using an adhesive tape, and putting little feed into the feed box, and training, by a food reward method, the poultry to recognize the red photographic paper; and when the poultry peck the red photographic paper, pushing, by the electric push rod, the feed box into the wooden testing box through the horizontal trough to allow the poultry to peck the little feed for 4 s, and then pulling, by the electric push rod, the feed box out of the wooden testing box to prevent the poultry from pecking the handful of little feed; or when the poultry peck the yellow photographic paper, disabling the electric push rod, and giving no feed reward; and removing the feed on the surface of each of the two color photographic papers after the poultry have correctly recognized the red photographic paper for three times, and then performing later training on the poultry; and 2.2) later training:

blocking the two color photographic papers by using one second black PVC backdrop, quickly removing the second black PVC backdrop after maintaining or reversing positions of the two color photographic papers, observing responses of the poultry to the two color photographic papers, and determining whether the poultry recognize and peck the red photographic paper; and repeating the training until the poultry recognize the red photographic paper for ten consecutive times;

3) Testing:

keeping the red photographic paper unchanged, and successively replacing the original yellow photographic paper with the RGB color (255, 255, 0) by a plurality of photographic papers whose G components in a RGB color space are sorted in descending order, to make colors of paired photographic papers gradually approximate to a red color; and after each replacement, performing the later training in step 2.2), repeating the testing for twelve times, and recording results of last ten times indicating whether the poultry accurately recognize the red photographic paper in the testing.

8. The lighting experimental method for reducing the ability of the poultry to recognize the red objects according to claim 7, wherein in the testing in step 3), RGB colors of the plurality of photographic papers whose G components in the RGB color space are sorted in descending order are (255, 219, 0), (255, 182, 0), (255, 146, 0), (255, 109, 0), (255, 73, 0), and (255, 36, 0), respectively.

9. The lighting experimental method for reducing the ability of the poultry to recognize the red objects according to claim 7, wherein before the training and the testing, the poultry are kept hungry.

10. The lighting experimental method for reducing the ability of the poultry to recognize the red objects according to claim 7, wherein the poultry comprise chickens.

* * * * *